United States Patent
Kaern

(10) Patent No.: US 8,201,689 B2
(45) Date of Patent: Jun. 19, 2012

(54) PACKAGE

(75) Inventor: Viggo Aaberg Kaern, Frederiksberg (DK)

(73) Assignee: Coloplast A/S, Humlebaek (DK)

( * ) Notice: Subject to any disclaimer, the term of this patent is extended or adjusted under 35 U.S.C. 154(b) by 186 days.

(21) Appl. No.: 12/828,302

(22) Filed: Jul. 1, 2010

(65) Prior Publication Data

US 2011/0000806 A1  Jan. 6, 2011

Related U.S. Application Data

(63) Continuation of application No. 10/352,181, filed on Jan. 28, 2003, now Pat. No. 7,770,728.

(30) Foreign Application Priority Data

Jan. 28, 2002 (DK) .................. 2002 00136
Nov. 4, 2002 (DK) .................. 2002 01690

(51) Int. Cl.
*B65D 83/10* (2006.01)

(52) U.S. Cl. .......................... 206/364; 206/815; 383/35

(58) Field of Classification Search .................. 206/363, 206/364, 438, 439, 484, 484.1, 815; 383/35, 383/210
See application file for complete search history.

(56) References Cited

U.S. PATENT DOCUMENTS

| | | | | |
|---|---|---|---|---|
| 2,998,880 | A * | 9/1961 | Ladd | 206/363 |
| 4,248,236 | A * | 2/1981 | Linder | 604/100.01 |
| 5,392,918 | A * | 2/1995 | Harrison | 206/571 |
| 5,497,601 | A * | 3/1996 | Gonzalez | 53/449 |
| 6,053,313 | A * | 4/2000 | Farrell et al. | 206/364 |
| 2010/0305527 | A1* | 12/2010 | Murray et al. | 604/328 |
| 2011/0056852 | A1* | 3/2011 | Frojd | 206/210 |

\* cited by examiner

*Primary Examiner* — Jacob K Ackun

(74) *Attorney, Agent, or Firm* — Coloplast Corp.; Daniel G. Chapik; Nicholas R. Baumann

(57) ABSTRACT

A package is described having two blanks of a sheet material joined along edges to form one or more enclosed compartments to retain a urinary catheter. The joined edges provide at least one peeling zone permitting separation of two foil walls. A gripping means is provided to allow a firm grip relative to the peeling zone.

7 Claims, 9 Drawing Sheets

PACKAGE

FIELD OF THE INVENTION

Figure 1:
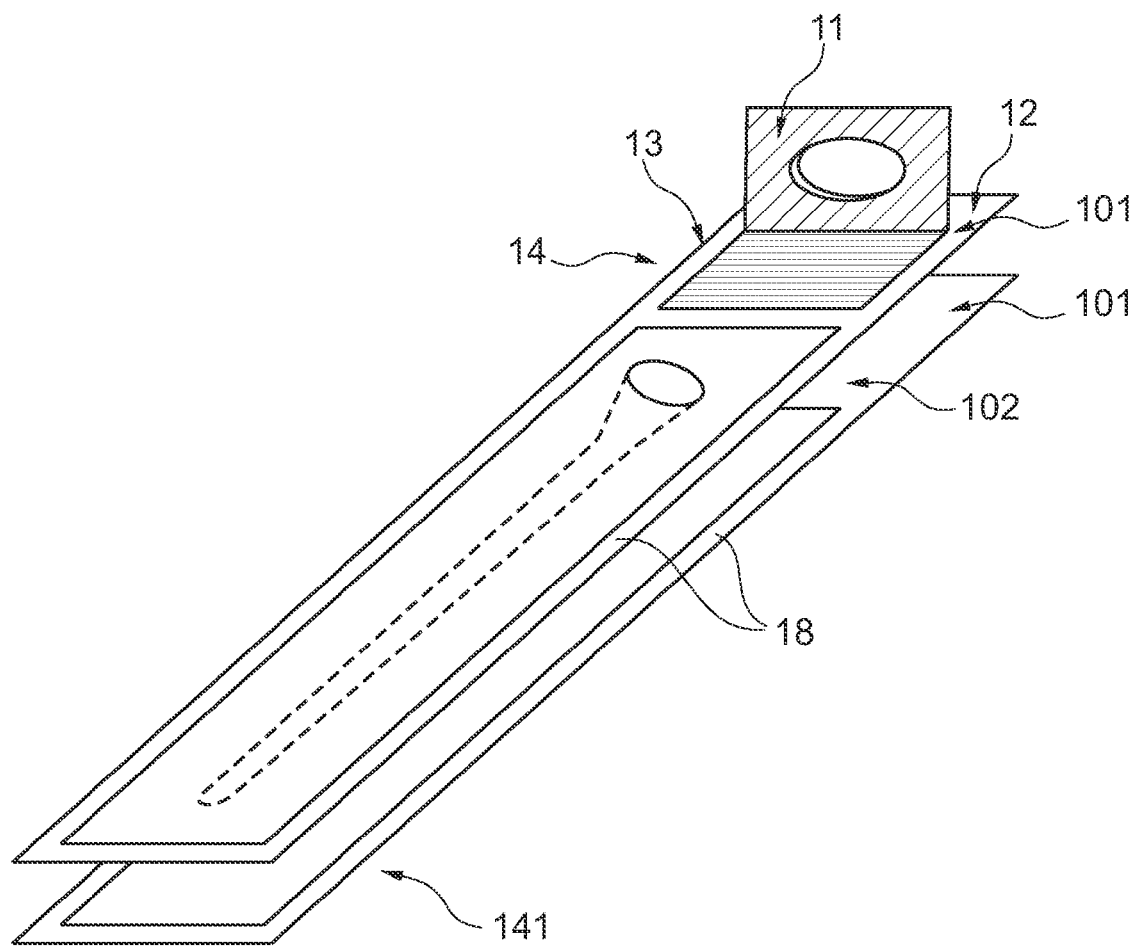

The invention relates to an easy to open package e.g. for medical utensils and in particular to a package of the kind comprising two joined blanks of a sheet material sealed by their peripheral ends, thereby constituting an enclosed compartment for a medical utensil.

BACKGROUND OF THE INVENTION

A package of this type is known from a variety of applications, e.g. for packing food products, household appliances or medical utensils. The package is usually made from two sheets of a flexible material joined by their peripheral edges to form an enclosure for the item in question.

Typically, medical utensils are designed for one-time use and, accordingly, the costs for producing, packing and sterilising the utensil is an important issue. Known packages are designed primarily with focus on the support for safe and sterile handling of utensils. Often, the package is designed with the presumption that full dexterity is available for the opening of the package.

Medical utensils such as needles, catheters and the like, are often to be used by a medical practitioner who, e.g. during surgery, is prevented from using both hands. Likewise, disabled individuals, such as para- or tetraplegics having reduced dexterity, use urinary catheters for unassisted draining of the bladder. Accordingly, individuals for whom removal of the medical utensil from the package may be difficult often use and thus has to unpack such utensils in their daily life.

WO 96/30277 discloses a method of non-contaminating use of a medical catheter directly from a package, i.e. insertion of the catheter into a body canal during the opening procedure of the package. The disclosed package comprises two joined foil blanks, sealed by their respective peripheral ends. The opening of the package is supported by the provision of a gripping flap, i.e. the joined foils terminate in a non-joined end-zone wherein the foils can be separated and from which zone the foils can be peeled apart. EP0629415 discloses a package holding a medical utensil under controlled environmental conditions. The package comprises a support member and a cover member. The product intended for package is placed on the supporting member and, subsequently, the flexible cover member is joined to the supporting member. The result is a sterile package for a medical appliance. Even though the disclosed package is provided with gripping means, opening may cause troubles for individuals having a reduced dexterity and in particular for individuals prevented from using both hands. In particular, it may be difficult to separate the foils for peeling the package open.

DESCRIPTION OF THE INVENTION

It is an object of a preferred embodiment of the present invention to provide a package with enhanced opening facilities and which allows easy opening even for individuals having a reduced dexterity.

Accordingly, a first aspect of the present invention relates to a package composed of a first and a second foil joined to each other by an edge-joint extending along all side edges of the foils so as to form a compartment for storage of an object between the foils and inside the edge-joint, wherein each foil defines an inner surface towards the other foil and an outer surface towards the ambient atmosphere, the edge-joint comprises at least one peeling zone permitting separation of the two foil walls, and at least the first foil comprises or defines a gripping means.

The first and second foil may be two separate foils or a single foil. In the latter case, the first and the second foils are preferably defined by folding the single foil and in preferred embodiment, where the longitudinal extension of the package is larger the width, the single foil is preferably folded either along a line extending in the longitudinal direction or in the cross-wise direction.

As indicated, the edge-joint comprises at least one peeling zone. This peeling zone constitutes in preferred embodiments the edge joint along all edges of the foils while the peeling zone constitutes the edge joint along a part of the side edges in other preferred embodiments. The later situation being especially useful when the package is to be opened only partly, for instance along half the length of the package.

An important preferred feature of preferred embodiments of the present invention is that the gripping means is(are) shaped so as to enable a firm grip without changing the position of the foils' inner surfaces relatively to each other. Preferably, a firm grip is considered to be one where the force needed to separate the foils in the peeling zone can be applied.

The gripping means is attached to or defined in the first foil, preferably in the vicinity of the peeling zone, thus the user can easily catch one of the foils and separate it from the other foil of the package. Accordingly, opening of the package is facilitated for the user having reduced dexterity. Preferably, the surface structure of the gripping means deviates from the surface structure of the foil. Moreover, the gripping means may be attached to the foil in a non-planar joint, i.e. the gripping means may be attached to the outer surface of the foil in a way allowing for easy gripping of the gripping element. In a preferred embodiment, the gripping means is constituted by a part of the foil extending in a direction outwardly from the package. The package may thus be made from one at least substantially plan foil and another non-plan foil, i.e. a foil which is folded outwardly at least one time, thus allowing the user to get a firm grip in the outwardly folded part.

The object in question, could be a medical utensil such as a catheter, a cannula, a needle, or any other kind of a medical utensil. The peeling zone, preferably, extends along all side edges in order to allow complete separation of the two foils during an opening procedure where the foils are peeled apart. Sealing, welding, gluing or any other methods of adhesively bonding two foils together may provide the edge-joint.

The width of the peeling zone is decided by the actual need depending on the product to be packaged. The package has two opposing ends, a first end and a second end. The first end of the package may as an example be adapted to house a proximal or insertable end of a needle or urinary catheter. As an example, the package may in this end be adapted for complete separation of the foils, thus allowing for the intended use of the utensil without removing the utensil from the package. In one embodiment, the package may have a rectangular shape, with two oblong sides between two opposing end-zones. Preferably, a gripping-zone is provided in one of these end-zones and, if the package accommodates a needle, an cannula or a urinary catheter, the proximal end thereof, i.e. the end adapted for insertion into a body canal, is preferably arranged in an end-zone provided with a gripping zone.

In the gripping zone, at least the first of the foils may be provided in a length so that it extends outside the edge-joint so as to define at least one tear-open flap of which the inner surface is accessible without peeling.

Preferably, the gripping means is an element which is attached to the foil, e.g. in the vicinity of the gripping zone or even more preferably, to the tear-open flap.

In order to further enhance the ability of the use to separate the foils or just to get a grip in one of the foils, the first foil could be provided with a through hole of a size allowing a finger-grip through the hole, the hole being provided in the tear-open flap.

In order to allow the user to open the package by use of only one hand, it may be an advantage to provide means for adhesively bonding the package to exterior objects, e.g. to a wall in the bathroom. Therefore, the second foil, i.e. the foil not provided with the gripping means may comprise an adhesive element, e.g. covered with a piece of protective back-paper. Prior to opening, the user removes the back-paper, adheres the package to a fixed object, e.g. to a wall, grips the gripping means and pulls the tear-open flap in order to peel the foils apart for opening the package. During this procedure, the user may in particular pull the tear-open flap in a direction substantially perpendicular to the oblong direction of the package.

In order to allow the user to even more easily grip the tear-open flap, the one foil which extends outside the edge-joint may comprise a through hole provided in the gripping zone or in the gripping element. The through hole should preferably be of a size allowing the user to grip through the hole with a finger. In order to allow finger-grip, the through hole could e.g. have a diameter in the range of 10-40 mm, such as in the range of 20-30 mm. Alternatively or additionally, the at least one foil which extends outside the edge-joint may be provided with a fold to support the grip. The package may thereby allow the opening of the package by placing one or more fingers in the through hole or by grasping the fold, and then by pulling the two foils apart.

Sometimes, it may be an advantage to provide the package with both of the two foils extending outside the edge-joint, thus forming two tear-open flaps. This allows the user to open the package by tearing the two flaps in mutually opposite directions. In this embodiment, it may be an advantage to provide the inner surface structure of the first foil differently from the inner surface structure of the second foil. As an example, the first foil may have embossing marks keeping the two foils apart and thus making it easier for the user to separate the two foils for tearing the package open. Another way of facilitating easy separation of the foils is to let one of the foils extend further outside the edge-joint than the other foil, i.e. providing two flaps of different size and/or different shape. The package may be provided with a gripping string constituted by a string which in at least one end is attached to one of the foils in the gripping zone.

A label attached to one of the foils in the gripping zone may also constitute the gripping means. In particular, if the gripping means is a label, the gripping means may advantageously be attached to the outer surface of one of the foils so that it covers or crosses over the edge-joint. The label may be softly adhered to the package in one-end, e.g. the end facing the intermediate part of the package while, at the opposite end, the label may be strongly adhered to the surface. The softly adhering of the label to the surface reduces the risk of unintended opening of one package. Prior to use, the end opposite the contact area is lifted free from the package and the gripping means is used for opening the package. As an example, one part of the label may be attached to the outer surface of one of the foils within the edge-joint and another part may be attached to the outer surface of one of the foils outside the edge-joint. Alternatively, the label may be attached only to the part of the outer surface located outside the edge-joint so that it extends along the outer surface across the edge joint without being attached to the part inside the edge-joint. The gripping means thus allows the user to separate the tear-open flaps by gripping the part of the label which is not attached to the foil. Subsequently, by pulling, the label is utilized to bend the tear-open flaps apart.

According to a preferred embodiment of the invention, the label comprises at least one and preferably two cut-lines which, when the label is attached to the outer surface of the foil, extends from an edge of the label. Preferably, the cut-line(s) starts at the edge from a position in the vicinity of the edge-joint and extends along the tear-open flap towards the end-zone of the gripping-zone. The cut-line(s) terminates within the label in a semi circular stop-portion. Due to the cut-line(s) one part which is less adhesively bonded or not bonded to the surface of the foil at all can be peeled partly off from the other part of the label which part is strongly adhesively bonded to the foil. Due to the stop portions, the separation of the two parts stops during the peeling, and the part which is partly peeled off may advantageously be used as a flap for tearing the two foils apart or as a flap for separating one of the foils from the other foil for tearing the package open. This opening procedure is in particular facilitated by a label which is adhesively bonded to the outer surface of the foil in the part located outside the edge-joint and where the label is not bonded to the outer surface in the part located inside the edge-joint. Preferably, the label has a through hole of a size allowing finger grip.

It is envisaged, that this label is not only applicable in connection with packages according to the present invention, but may advantageously be applied to many kind of devices where a handle is needed.

In a further embodiment the gripping means is attached to the inside of the first foil and wherein the gripping means extend outside the edge-joint, i.e. the gripping means is adhered to the inside of the first foil substantially stronger than to the inside of the second foil, to which it is adhered only through the edge-joint. Thus when a user tears the gripping means hard enough for the package open, i.e. the edge-joint to break the gripping means is still attached to the inside of the first foil, and the package may be opened by further tearing.

Furthermore, the package may form a plurality of enclosed spaces for a plurality of medical utensils.

DETAILED DESCRIPTION OF THE INVENTION

Figure 2:
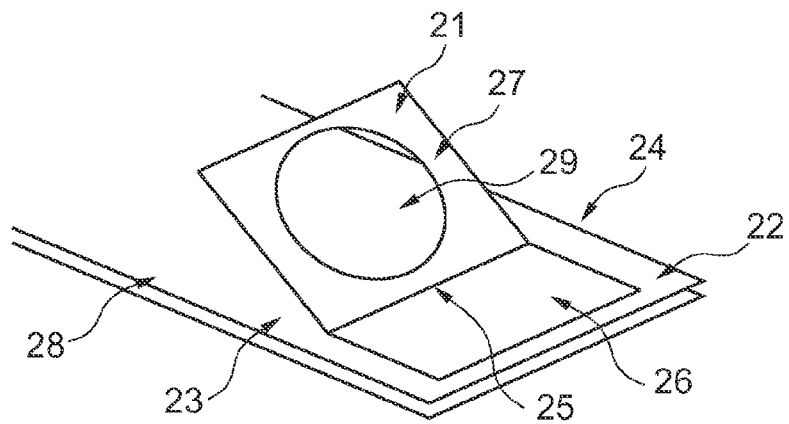
Figure 3:
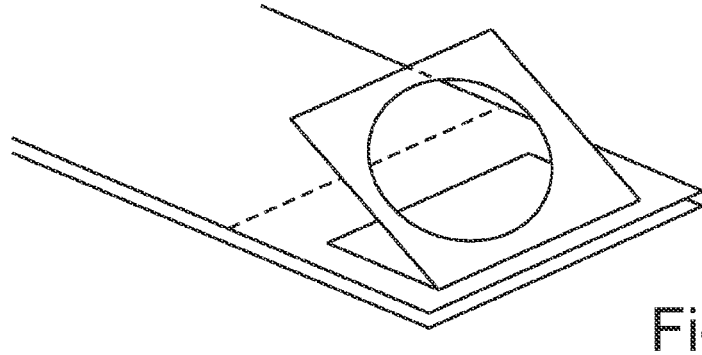
Figure 4:
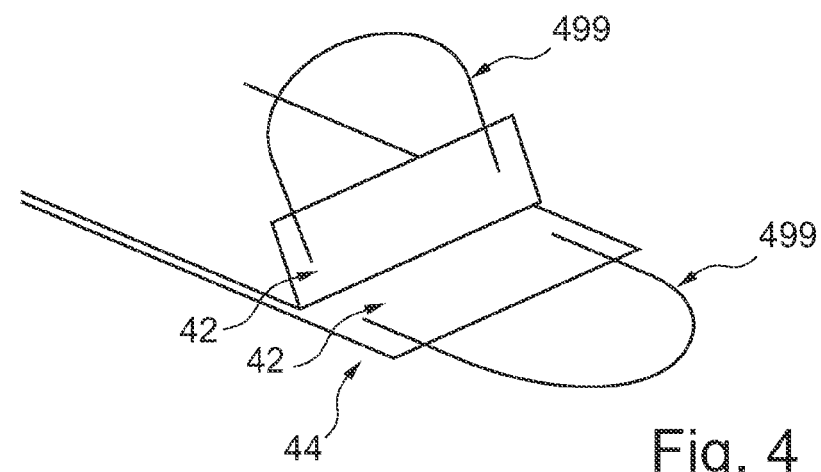
Figure 5:
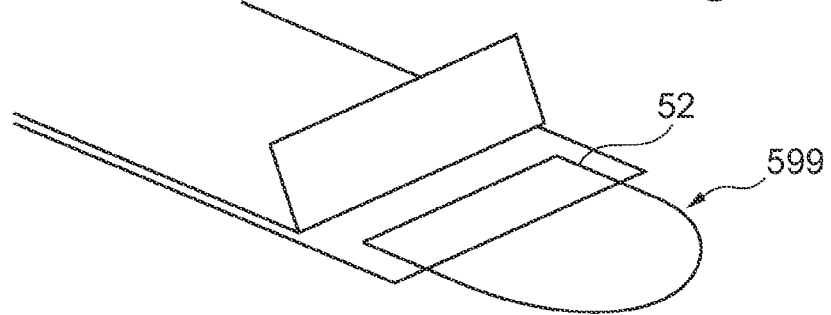
Figure 6:
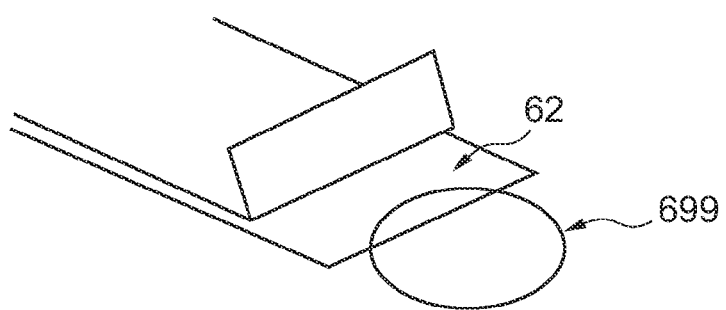
Figure 7:
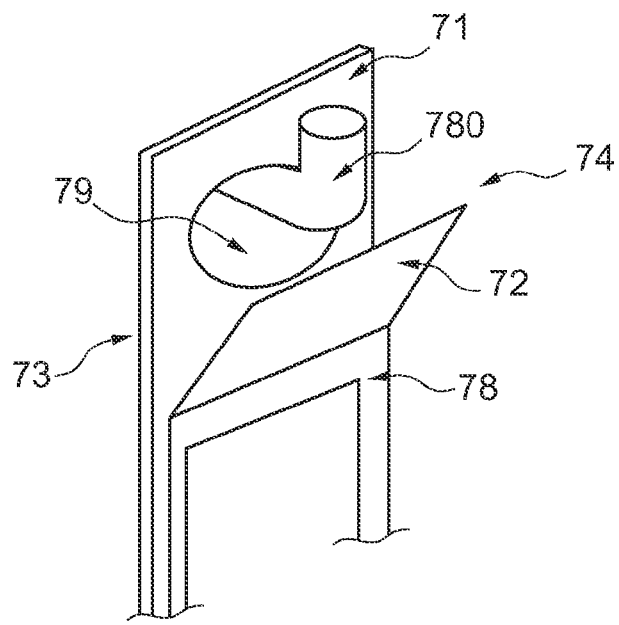
Figure 8:
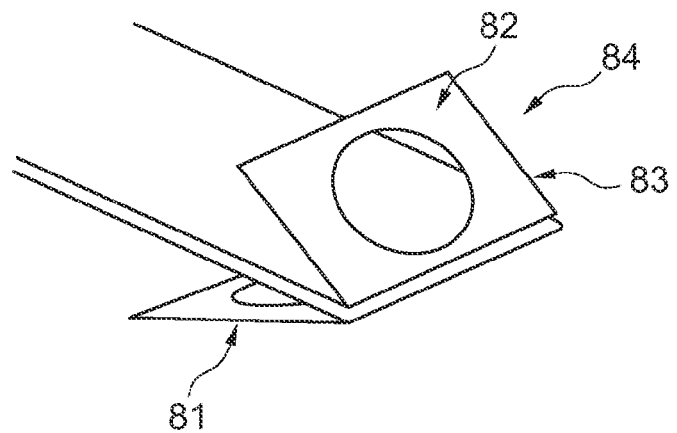
Figure 9:
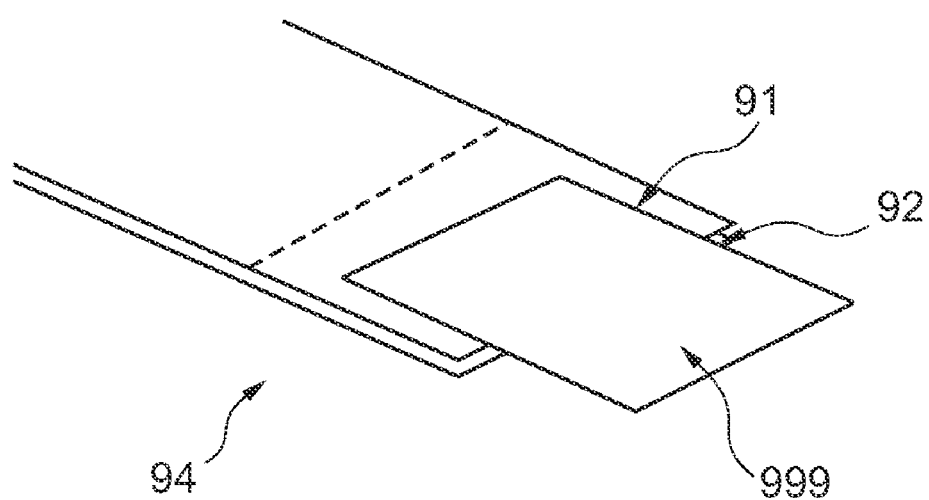
Figure 10:
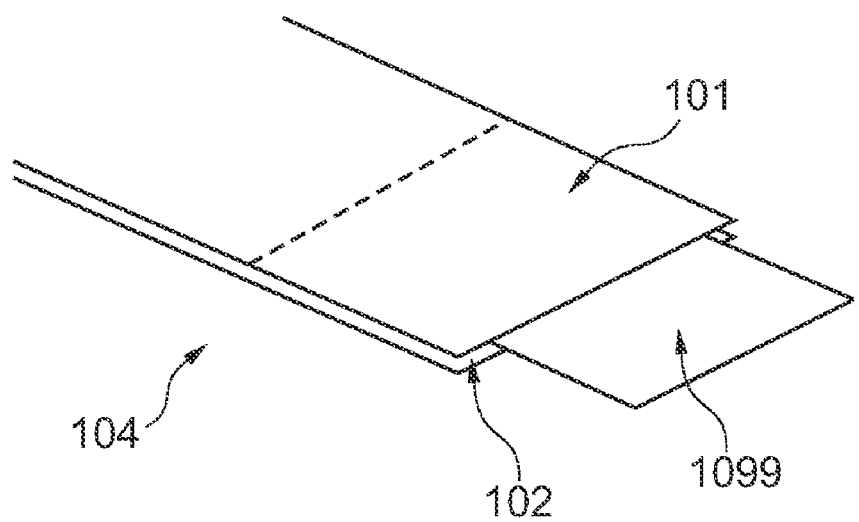
Figure 11:
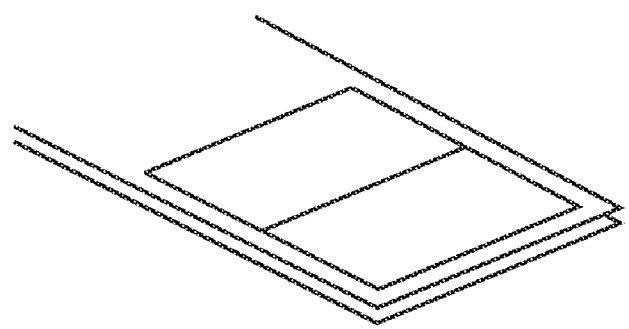
Figure 12:
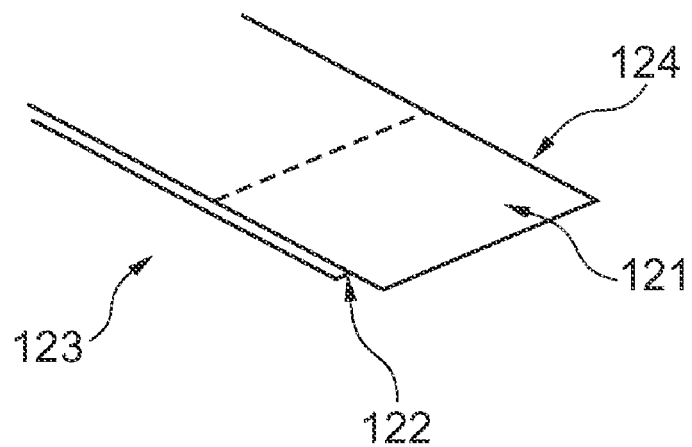
Figure 13:
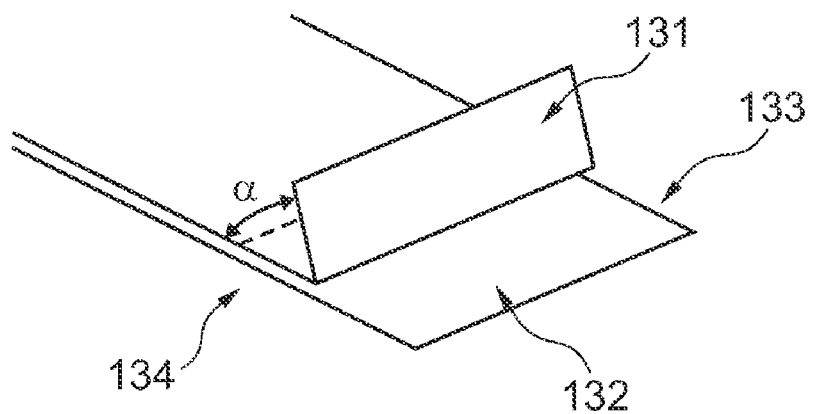

Preferred embodiments of the invention will now be described in details with reference to the drawing in which:

FIG. 1 shows an exploded view of a catheter package according to the present invention, FIG. 2 shows an elevated perspective view of an opening mechanism comprising a gripping means attached to a tear open flap according to the present invention, FIG. 3 shows an elevated perspective view of the opening mechanism comprising another embodiment of a gripping means attached to a tear open flap according to the present invention, FIG. 4 shows an elevated perspective view of the opening mechanism comprising a gripping string attached to a tear open flap according to the present invention, FIG. 5 shows an elevated perspective view of another embodiment of the opening mechanism comprising a gripping string, attached to a tear open flap, according to the present invention, FIG. 6 shows an elevated perspective view of yet another embodiment of the opening mechanism comprising a gripping string, attached to a tear open flap, according to the present invention, FIG. 7 shows an elevated perspective view of a medical utensil package, the package being suspended on a hook, or the like, through an opening in a tear open flap, according to the present invention, FIG. 8 shows an elevated perspective view of another embodiment of the opening mechanism, provided with openings in both tear open flaps in the gripping zone, according to the present invention, FIG. 9 shows an elevated perspective view of an opening mechanism comprising an element joined to a tear open flap, FIG. 10 shows an elevated perspective view of an opening mechanism comprising an element joined to a tear open flap, the element being joined to the tear open flap on the surface of the flap facing inside against the opposite flap of the package, FIG. 11 shows an elevated perspective view of a gripping means joined to a tear open flap, the element being folded in a direction extending from the first end zone towards the second end zone, according to the present invention, FIG. 12 shows an elevated perspective view of an opening mechanism wherein the first tear open flap extends beyond the second tear open flap in a direction facing away from the second end zone according to the present invention, FIG. 13 shows an elevated perspective view of an opening mechanism wherein the first tear open flap is folded in a direction facing the second end zone, according to the present invention.

Figure 14:
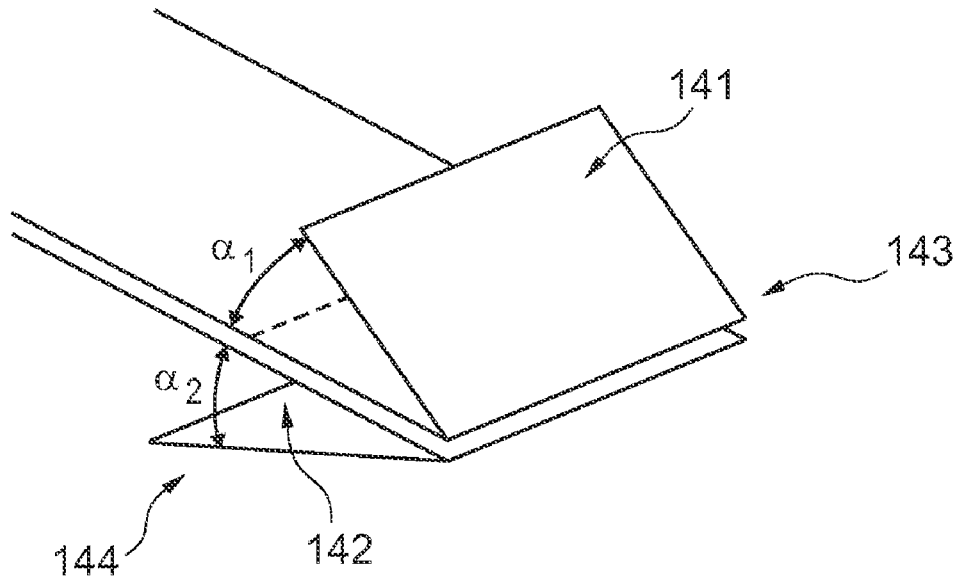
Figure 15:
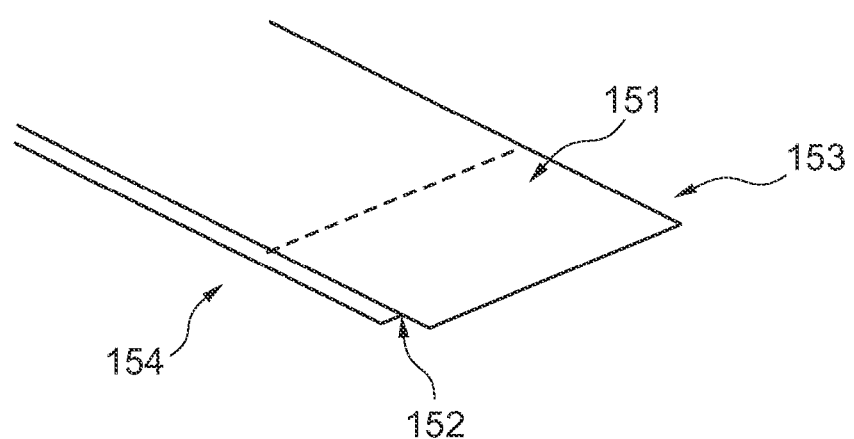
Figure 16:
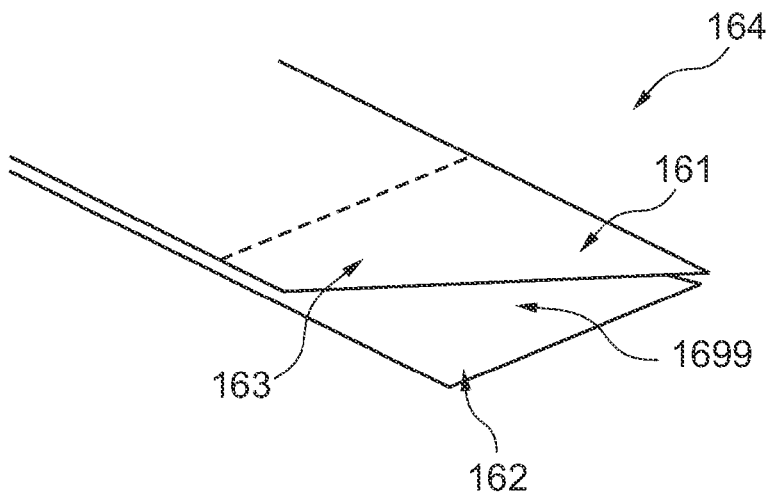
Figure 17:
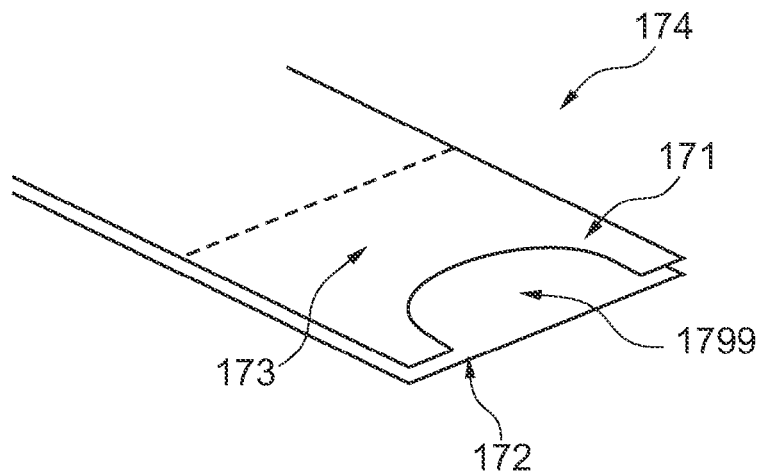
Figure 18:
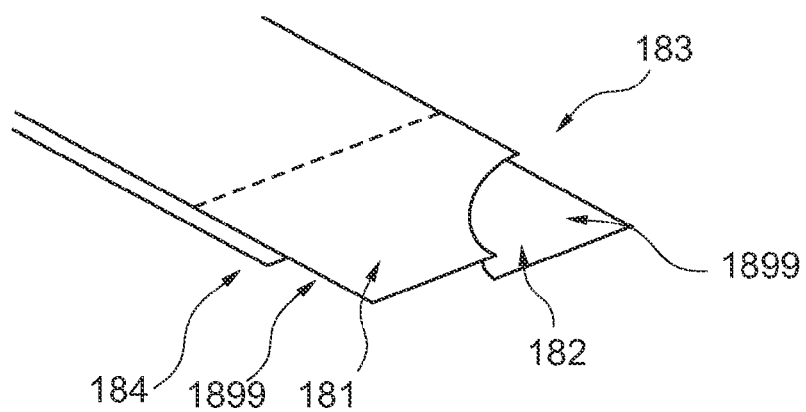
Figure 19:
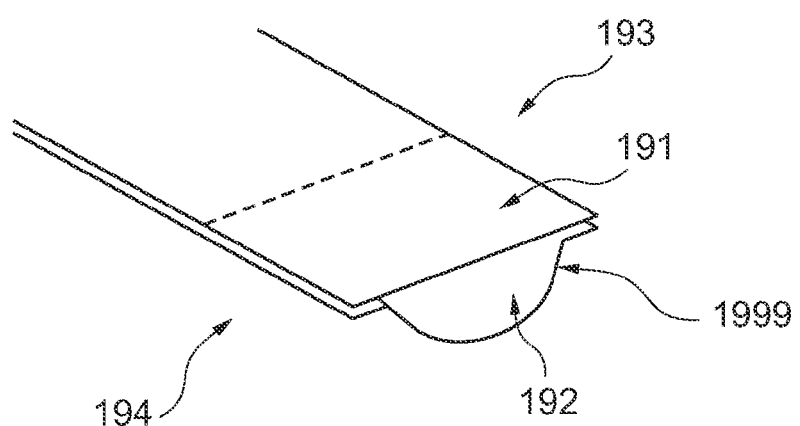
Figure 20:
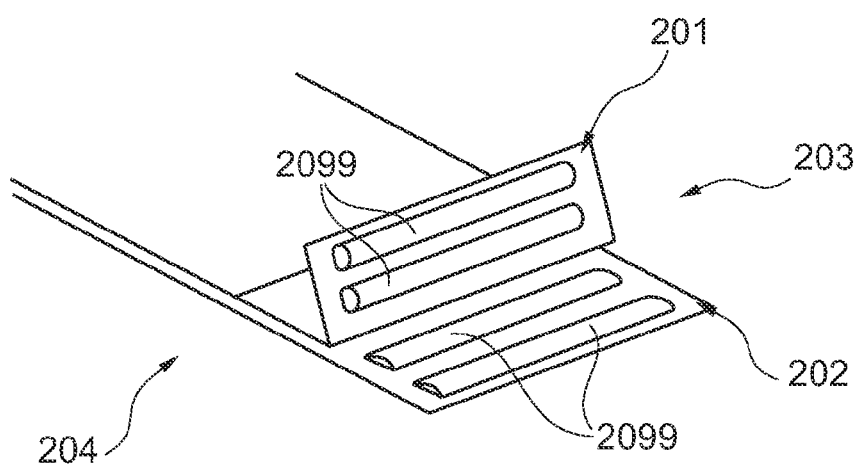
Figure 21:
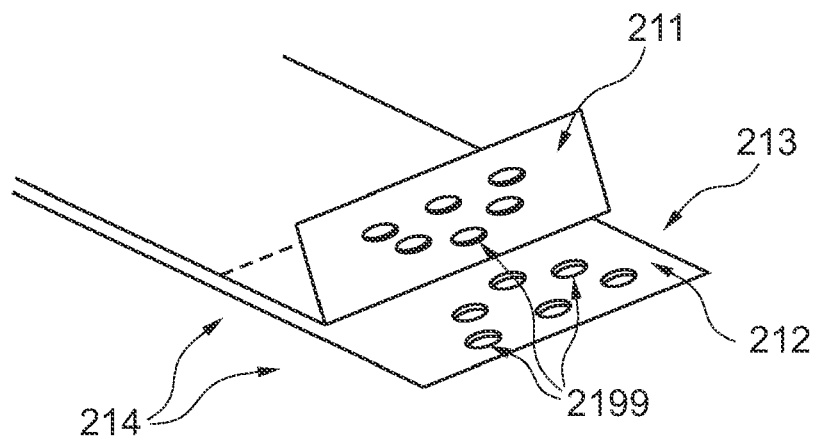
Figure 22:
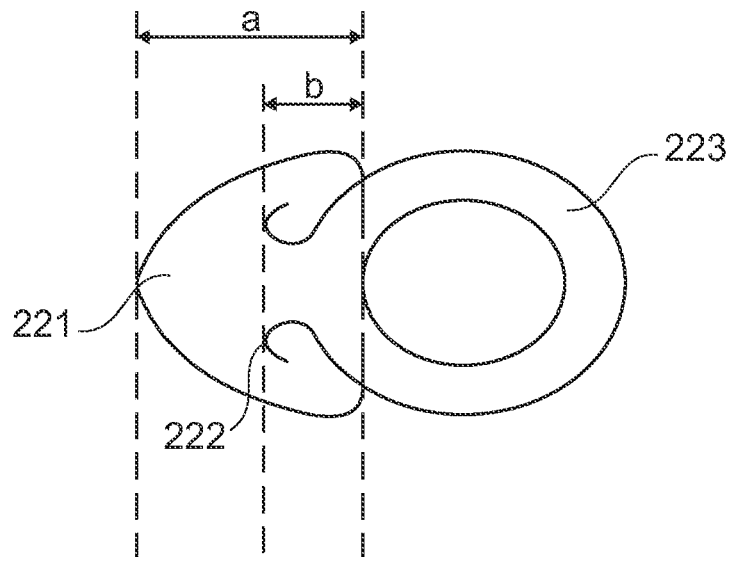

FIG. 14 shows an elevated perspective view of an opening mechanism wherein both the first and the second tear open flaps are folded in a direction facing towards the second end zone, according to the present invention, FIG. 15 shows an elevated perspective view of an opening mechanism wherein the first tear open flap extends beyond the second tear open flap in a direction facing away from the second end zone according to the present invention, FIGS. 16 and 17 show an elevated perspective view of an opening mechanism wherein the first tear open flap is provided with an extended area in relation to the second tear open flap, FIG. 18 shows an elevated perspective view of an opening mechanism wherein the first and the second tear open flaps have cut-outs according to the present invention, FIG. 19 shows an elevated perspective view of an opening mechanism wherein the second tear open flap forms a convexity, FIG. 20 shows an elevated view of an opening mechanism wherein the first and second tear open flaps have a plurality of convexities. The convexities on the first rear open flap face the second tear open flap, and the convexities on the second tear open flap face the first, FIG. 21 shows an elevated view of an opening mechanism characterised in that the first and second tear open flap have a plurality of openings, and FIG. 22 shows a gripping means according to the invention.

Figure 23:
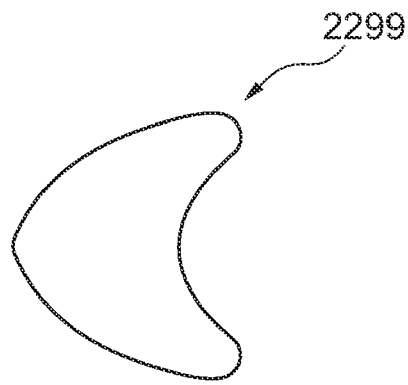

FIG. 23 shows an adhesive mark to be attached to one side of the catheter package and allowing the package to be adhered to a wall surface.

Referring to FIG. 1, a package for a catheter according to a preferred embodiment of the invention has two foil blanks (101), forming a enclosed compartment (102) adapted to store an elongated member, such as a catheter, the foil blanks further defining a first (14) and a second (141) end zone, a peeling zone (18) comprised in the outer peripheral part of the sealed foil blanks, a tear open flap (12) defined by a portion of the foil blanks extending beyond the peeling zone (18), and a gripping means (11) connected to the tear open flap (12). The area extending beyond the peeling zone (18) forming tear open flaps is defined as a gripping zone (13). The catheter may be arranged with either the insertable end or the connector end in the first end zone.

During use the package may first be adhered to an exterior object by an adhesive label positioned on the backside of a tear open flap (12) (see e.g. FIG. 23). The flaps may be bent backwards, i.e. away from the side where the adhesive label is positioned. When the flaps are bent the back paper of the label (silicone paper) releases in that end which is closest to the catheter. This render it possible to remove the back paper, e.g. with a finger or the mouth, since there is now space between the back paper and the adhering zone of the label. When the back paper is removed, the package is fixed to a sink or a wall by the adhesive label. An even better adhesion will be obtained if the adhesive label is attached to a horizontal surface and with the rest of the package hanging straight down above an edge.

The back paper is released from the adhering zone due to the design of the adhesive label. The area (adhering width) is reduced in one end, and a peeling is obtained with a low applied force. The back paper (silicone paper) is stiff, and since the stiffness of the silicone paper is height with respect to the adhesion force towards the adhering zone, the silicone paper will not follow the curvature of the label when the package is bent.

When the package has been fixed, a finger is pushed trough the hole of the gripping means (11) which is positioned on the other flap than the flap with the adhesive label. The best result of opening the package will usually be obtained by sticking the finger up through the hole from the lower side. With the finger positioned in the hole, the gripping means should be pulled perpendicularly away from the wall. First the gripping means is freed from the package. Additional pulling in the gripping means will result in that the package is opened along the edge-joint. The pulling direction should be changed such that the angle between the vertical and the pulling direction is around 45 degrees. The pulling continues until the package is sufficiently opened (according to liking and need), typically from 50 to 120 mm. When the package is open the finger is withdrawn from the gripping means, and the catheter may be taken out of the package and used.

The catheter is used. After usage the catheter may be reinserted into the package.

The package can be removed from where it was adhered. If the package is adhered to a vertically extending surface, e.g. a wall, the user should grab the package anywhere below the adhering zone and pull while tilting the package upwardly (the pulling angle should preferably be between 45 and 90 degree with respect to vertical). The adhering zone is released from the exterior object due to the action. If the package is placed at an edge with the adhering zone attached to a horizontal surface, the user should grab the part hanging down from the edge as highly as possible and lift the package vertically upwards. The adhering zone is released from the exterior object due to the action.

The catheter is thrown away.

By using aforesaid method, the risk of spilling any liquid is reduced.

FIG. 2 shows a perspective view of a gripping means (21), in the form of a label, attached to a tear open flap (22), the gripping means is preferably joined to a surface of the gripping zone (23) in the first end (24) zone, the gripping means is folded (25) transversely so as to define a contact area (26) for a joint, an area for providing a gripping surface (27). The gripping means is joined to the tear open flap in the gripping zone, by its contact area so that the transverse folding line is positioned outside of the peeling zone at a distance in the range of 10-100 mm such as in the range of 20-80 mm, such as in the range of 40-60 mm, from the joint (28). The gripping means is further provided with an opening(29) of finger size so as to provide for finger gripping of the element. The gripping means can be used both as an aid to open the package and for as an aid to separate the tear open flaps. The gripping means may be softly adhered to the package in the end opposite the contact area (26) so that the element, e.g. during storage of the package, stays in close contact with the package. This reduces the risk of unintended opening of one package. Prior to use, the end opposite the contact area is lifted free from the package and the gripping means is used for opening the package.

It is an advantage to provide the catheter package in a material which is at least substantially gas and water impermeable and which is durable to at least moderate external conditions, such as temperature variations and light. The material should at least substantially maintain its properties over a period of up to 12 or more months, e.g. up to 24 month. The catheter package or at least the foil blanks may therefore preferably be made from silicone or a thermoplastic elastomeric material, other thermoplastic materials, curable elastomeric materials, polyamide resins or elastomers or any mixture thereof, i.e. the group may comprise materials like, PA, PP, PVC, PU, PE, latex, and/or Kraton™. All parts of the catheter package may be made from two foils of a sheet material joined along edges, e.g. by melting or gluing the foils together or the package may be made from an extruded substantially tubular member being closed in both ends. The two foils or blanks of a sheet material constituting the package may be provided by bending or folding one blank of a sheet material and by welding the edges together, thus forming an envelope for the catheter. The foil may advantageously be made from laminates of different materials. One layer may e.g. be a layer of aluminium or similar metal for provision of a completely gas-impermeable package. The two blanks of sheet material may be provided in two different materials.

FIG. 3 shows another embodiment of the gripping means described in FIG. 2. The gripping means is rotated 180 degrees in relation to the gripping means in FIG. 2.

FIG. 4 shows an alternative embodiment of a gripping means attached to a tear open flap (42). The gripping means is in this embodiment constituted by at least one string (499). The string is fastened by its ends to the tear open flap (42) in the gripping zone (44), thereby providing for an opening of finger size.

FIGS. 5 and 6 show an alternative embodiment of the gripping means described in FIG. 4, only one gripping string (599,699) is attached to the one tear open flap(52,62). The string further being without open ends.

The strings described in FIGS. 4,5 and 6 are preferably made of a flexible or rigid material, e.g. the same material as mentioned for the package itself. A flexible material will render the possibility of using one or more fingers, since the opening can be expanded. The string is fastened by its ends to the tear open flap by means of gluing, taping, or welding.

FIG. 7 shows a view of a first end zone (74) of a catheter package, a first and a second tear open flap (71),(72) in a gripping zone (73), a peeling zone (78) and a hook (780) for suspension of the package. The first of the tear open flaps is provided with an opening (79), The catheter package is suspended on the hook (780) through the opening (79) in the first tear open flap (71). The step of suspending the catheter package on the hook causes the hook to force the second tear open flap (72) to fold in a direction away from the hook, whereby a separated space is created between the both tear open flaps.

The separated space gives direct access to the inside of the tear open flaps, hence a first step of separating the tear open flaps by hand can be eliminated. The opening can optionally be reinforced by a label of equal size of the tear open flaps. The label is fastened by means of gluing or welding. The label is provided with an opening corresponding to the opening of the gripping zone(23). Optionally, the reinforcement label can be made of double-sided adhesive material, thereby providing means for both adhering the package and to a flat surface. FIG. 23 shows a label adhering the package to a flat wall surface. The label could be made e.g. from a 150 mm. PE sheet material with a permanent UV acrylic adhesive. The label could be provided with a kautsjuk based glue both on the side facing the package and on the side facing the flat wall surface. Preferably, the label is covered with a piece of silicone paper which can easily be pealed of prior to use. In general the label could have any shape but a shape defining tip-points (2299). The shape of the label which is disclosed in the FIG. 23 further enables easy pealing of the cover paper.

FIG. 8 shows a view of a first end zone(84) of a catheter package, a first(81) and a second(82) tear open flap in a gripping zone(83). Both tear open flaps are folded in a direction facing a second end zone, the tear open flaps are further provided with through holes of finger size, so as to provide for finger gripping of the tear open flaps. There are two through holes provided for so as to render a possibility of using the force of a users both hands to open the package. Optionally the first tear open flap can be suspended on a hook, whereby the second is used for pulling away the foil blank with the use of a hand. Another option of using fabrication is to displace the centre of the two holes in relation to each-other. This would render the benefit of giving direct access to the inside if the foil blanks.

FIGS. 9 and 10 show a view of a first end zone(94,104) of a catheter package, a first(91,101) and a second(92,102) tear open flap in a gripping zone(94,104). A gripping element (999,1099) is joined to the one of the tear open flaps. The gripping means can be fastened on the outside of the tear open flaps(FIG. 11) or on the inside of the tear open flaps(FIG. 12) The gripping means can optionally be made from a more rigid material then the tear open flaps. In a user situation when the gripping means is bent in one direction whilst holding the remainder of the package at a steady position, the tear open blanks will be separated.

FIG. 11 shows a view of a catheter package as shown in FIGS. 2 and 3, but without the through hole.

FIGS. 12 an 15 show a view of a first end zone (124,154) of a catheter package, a first(121,151) and a second(122,152) tear open flap in a gripping zone(123,153), wherein one of the tear open flaps extends beyond the other tear open flap, hence direct access to the inside of the tear open flaps is provided for.

FIG. 13 shows a view of a first end zone (134) of a catheter package, a first (131) and a second (132) tear open flap in a gripping zone(133), wherein one of the tear open flaps is folded transversally in a direction facing the second end zone. The angle α between the transversally folded flap and the outer surface of the foils is preferably selected to be between 90 and 45 degrees, preferably between 75 and 45 degree, in order to provide a firm grip. However, the angle α may also be selected between 135 and 45 degrees. Furthermore, especially in embodiments, where the tear open flaps are folded in general, the angle α between the folded flap and the outer surface of the foils is preferably selected to be smaller than 180, such as smaller than 175, even smaller than 170 such as smaller the 165, preferably smaller than 130, such as smaller than 110, even smaller than 90, such as smaller 70, preferably smaller than 60, even smaller than 50, such as smaller than 40, such as smaller than 30, preferably smaller than 20, even smaller than 15, such as smaller than 10, preferably smaller than 5 degrees. Furthermore, embodiments where the folded flap is flush with the foil, that is where the angle is substantially equal to zero, may be preferred.

FIG. 14 shows a view of a first end zone (144) of a catheter package, a first (141) and a 35 second (142) tear open flap in a gripping zone (143), wherein both tear open flaps are folded transversally to extend in a direction facing the second end zone. The angles $\alpha_1$ and $\alpha_2$ are selected similar to the angle $\alpha$ shown in FIG. 13, i.e. selected to be between 135 and 45 degrees, such as between 90 and 45 degrees, preferably between 75 and 45 degrees, or even between 135 and 45 degrees, in order to provide a firm grip. It is envisaged that the angles $\alpha_1$ and $\alpha_2$ may be different. Furthermore, in embodiments where the flaps are folded in general, each of the angles $\alpha_1$ and $\alpha_2$ may be selected to be within the limits stated above in accordance with the description of the embodiment shown in FIG. 13.

It is noted in this connection that in all the embodiments disclosed herein and embodiments falling within the scope of the present invention, wherein one or more flap is folded. e.g. folded during manufacture, the angle between the transversely folded flap or the flap in general and the outer surface of the foils is preferably selected to be within the limits stated above in accordance with the description of the embodiment shown in FIG. 13.

FIGS. 16 and 17 show a view of a first end zone (164,174) of a catheter package, a first (161,171) and a second (162,172) tear open flap in a gripping zone (163,173), wherein a portion of a first tear open flap (161,171) has been cut away. The cut-away gives direct access to the inside of the tear open flaps, whereby easy separation is achieved.

FIG. 18 shows a view of a first end zone (184) of a catheter package, a first (181) and a second (182) tear open flap in a gripping zone (183), wherein a portion of both the first and the second tear open flap has been removed. The cut-away portion (1899) in the each respective tear open flap has been arranged so that the cut-away portion of one flap gives direct access to the inside of the other flap, whereby easy separation is achieved.

FIG. 19 shows a view of a first end zone (194) of a catheter package, a first (191) and a second (192) tear open flap in a gripping zone (193), wherein the one tear open flap comprises a convexity (1999), the convexity extends from a centre between the first (191) and the second (192) tear open flap outwards from the package. Other bulging shapes than the convexity (1999) can as an alternative be applied to the tear open flap to ease separation of the flaps.

FIG. 20 shows a view of a first end zone (204) of a catheter package, a first (201) and a 35 second (202) tear open flap in a gripping zone (203), wherein the first and the second tear open flap have a plurality of bulges or convexities (2099) facing each-other on the inside. The one or more convexities keep the two tear open flaps at a separated position, hence easier access to the inside of the tear open flaps is provided for.

FIG. 21 shows a view of a first end zone (214) of a catheter package, a first (211) and a second (212) tear open flap in a gripping zone (213), wherein the first and the second tear open flap have a plurality of through holes (2199). The through holes aim to provide for an increased friction when gripped between two fingers. An optional feature would be to laminate the tear open flaps with a high-friction material so as to achieve the same function FIG. 22 shows a preferred embodiment of the gripping means. The gripping means is adhered to the package by a fixedly adhering part (221). In a preferred of a package the pointing part (a) of the adhesive part is pointing away from the package, i.e. towards the closer end of the package. The pulling part of the gripping means comprise a ring (223) which is not adhered, or only adhered weakly and/or partly to the package, so that it may be easily detached from the foil and be bent away from the package for a firmer grip. The adhesive part and the ring form a single element connected by a middle piece (b). The joint between the adhesive part and the middle piece comprise cut-lines. These cut-lines are terminating in semicircular stop-portions with a radius of curvature of approximately being between 0, 1 and 10 mm, such as between 1 and 5 mm or being between 2 and 3 mm. In a particular preferred embodiment the radius of curvature is approximately 1 mm. The cut-lines ensure that when pulling in the ring, the pulling force is applied in the plane of the adhering part. The width of the gripping means can be adapted to the use of interest, e.g. for allowing gripping with one or more fingers or even a hand. A typical width is accordingly preferably between 10-100 mm, such as between 10 and 100 mm or preferably between 20 and 35 mm. In a particular preferred embodiment the width is approximately 25 mm.

During use, the package may be suspended on a hook or via the adhesive label shown in the FIG. 23. In case the package is of the kind provided with an adhesive label, the protective silicone paper may easily be removed by bedding the package slightly whereby the paper will be separated from the tip points and thus easing the removal. Subsequently, the user will grip the gripping means (21) or the tear open flap (22) and pull the foils apart. Since the package is suspended on a hook or on the wall, or via the adhesive label the operation of opening the package may easily be performed.

Gripping means (e.g. as the one of FIG. 22) and adhesive label (e.g. as the one of FIG. 23) are in preferred embodiments placed on opposite sites of a package. As an alternative, two gripping means can be placed on opposite sites of a package to enable opening of the package by using two hands/fingers.

What is claimed is:

1. A package for a urinary catheter, the package comprising:
   a first foil attached to a second foil along a peripheral seal to form an enclosed compartment sized to retain the urinary catheter, each of the first foil and the second foil including a flap that extends past the peripheral seal to a free end; and
   a gripping element having a first portion that is attached to the flap of the first foil and a gripping portion that extends from the first portion of the gripping element that is movable relative to the first foil, the gripping portion defining a hole sized to receive a finger tip that facilitates opening the peripheral seal through separation of the first foil from the second foil.

2. The package of claim 1, wherein the first portion is attached to the flap nearer to the free end of the flap than to the peripheral seal.

3. The package of claim 1, wherein the gripping portion is pressed flat against the first foil in a delivery state and movable away from the first foil in a package access state.

4. The package of claim 1, wherein the gripping portion is unattached to an outer surface of the first foil.

5. The package of claim 1, wherein the gripping portion is removably bonded to an outer surface of the first foil.

6. The package of claim 1, wherein the gripping portion and the hole combine to form a pull ring.

7. The package of claim 1, wherein the gripping element is an adhesive label with the first portion adhesively attached to the flap of the first foil and the gripping portion unattached and movable relative to the first foil.

* * * * *